United States Patent
Ng et al.

(10) Patent No.: US 12,018,046 B2
(45) Date of Patent: Jun. 25, 2024

(54) USE OF CATION-EXCHANGE CHROMATOGRAPHY IN THE FLOW-THROUGH MODE TO ENRICH POST-TRANSLATIONAL MODIFICATIONS

(71) Applicant: Biogen MA Inc., Cambridge, MA (US)

(72) Inventors: Austen Ng, Watertown, MA (US); Robert S. Gronke, Boston, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 17/718,116

(22) Filed: Apr. 11, 2022

(65) Prior Publication Data

US 2022/0306684 A1    Sep. 29, 2022

Related U.S. Application Data

(63) Continuation of application No. 15/116,456, filed as application No. PCT/US2015/014469 on Feb. 4, 2015, now abandoned.

(60) Provisional application No. 61/935,728, filed on Feb. 4, 2014.

(51) Int. Cl.
  *C07K 1/18* (2006.01)
  *C07K 14/715* (2006.01)
  *C07K 14/755* (2006.01)

(52) U.S. Cl.
  CPC ............ *C07K 1/18* (2013.01); *C07K 14/7151* (2013.01); *C07K 14/755* (2013.01); *C07K 2319/30* (2013.01)

(58) Field of Classification Search
  None
  See application file for complete search history.

(56) References Cited

U.S. PATENT DOCUMENTS

| | | | |
|---|---|---|---|
| 4,757,006 A | 7/1988 | Toole et al. | |
| 4,868,112 A | 9/1989 | Toole et al. | |
| 5,004,804 A | 4/1991 | Kuo et al. | |
| 5,112,950 A | 5/1992 | Meulien et al. | |
| 5,171,844 A | 12/1992 | Van et al. | |
| 5,198,349 A | 3/1993 | Kaufman et al. | |
| 5,250,421 A | 10/1993 | Kaufman et al. | |
| 5,543,502 A | 8/1996 | Nordfang et al. | |
| 5,595,886 A | 1/1997 | Chapman et al. | |
| 5,610,278 A | 3/1997 | Nordfang et al. | |
| 5,789,203 A | 8/1998 | Chapman et al. | |
| 5,919,766 A | 7/1999 | Oesterberg et al. | |
| 5,972,885 A | 10/1999 | Spira et al. | |
| 6,048,720 A | 4/2000 | Dalborg et al. | |
| 6,060,447 A | 5/2000 | Chapman et al. | |
| 6,228,620 B1 | 5/2001 | Chapman et al. | |
| 6,316,226 B1 | 11/2001 | Van Ooyen et al. | |
| 6,346,513 B1 | 2/2002 | Van Ooyen et al. | |
| 6,458,563 B1 | 10/2002 | Lollar et al. | |
| 7,041,635 B2 | 5/2006 | Kim et al. | |
| 7,138,505 B1 | 11/2006 | Kuo et al. | |
| 7,300,773 B2 | 11/2007 | Drapeau et al. | |
| 7,404,956 B2 | 7/2008 | Peters et al. | |
| 2004/0186277 A1 | 9/2004 | Roemisch et al. | |
| 2008/0076155 A1 | 3/2008 | Fung | |
| 2010/0081615 A1 | 4/2010 | Pan et al. | |
| 2010/0311952 A1 | 12/2010 | Falkenstein et al. | |
| 2011/0046060 A1 | 2/2011 | Schellenberger et al. | |
| 2011/0046061 A1 | 2/2011 | Schellenberger et al. | |
| 2011/0098452 A1 | 4/2011 | Roy et al. | |
| 2013/0017997 A1 | 1/2013 | Schellenberger et al. | |
| 2013/0108629 A1 | 5/2013 | Dumont et al. | |
| 2013/0202595 A1 | 8/2013 | Pierce et al. | |
| 2016/0347787 A1 | 12/2016 | Ng et al. | |

FOREIGN PATENT DOCUMENTS

| | | |
|---|---|---|
| CN | 102066417 A | 5/2011 |
| EP | 0295597 A2 | 12/1988 |
| JP | 2011-502161 A | 1/2011 |
| JP | 2013-500711 A | 1/2013 |
| WO | WO 87/04187 A1 | 7/1987 |
| WO | WO 88/00831 A1 | 2/1988 |
| WO | WO 91/09122 A1 | 7/1991 |
| WO | WO 2007/046631 A1 | 4/2007 |
| WO | WO 2009/058812 A1 | 5/2009 |
| WO | WO 2010/071208 A1 | 6/2010 |
| WO | WO 2011/012726 A2 | 2/2011 |
| WO | WO 2011/015926 A1 | 2/2011 |
| WO | WO 2013/009526 A1 | 1/2013 |
| WO | WO 2013/153497 A1 | 10/2013 |
| WO | WO 2013/185114 A2 | 12/2013 |
| WO | WO 2015/120056 A1 | 8/2015 |

OTHER PUBLICATIONS

International Search Report and Written Opinion for International Application No. PCT/US2015/014469, dated May 8, 2015, 11 pages.

International Preliminary Report on Patentability for International Application No. PCT/US2015/014469, dated Aug. 9, 2016, 8 pages.

Eaton, D.L., et al., "Construction and Characterization of an Active Factor VIII Variant Lacking the Central One-Third of the Molecule," Biochemistry 25(26):8343-8347, American Chemical Society, United States (1986).

Freedman, S.J., et al., "Identification of the Phospholipid Binding Site in the Vitamin K-dependent Blood Coagulation Protein Factor IX," The Journal of Biological Chemistry 271(27):16227-16236, American Society for Biochemistry and Molecular Biology, United States (1996).

(Continued)

*Primary Examiner* — Marsha Tsay

(74) *Attorney, Agent, or Firm* — Wolf, Greenfield & Sacks, P.C.

(57) ABSTRACT

The present invention relates to improved methods in the separation recombinant polypeptides with post-translational modifications from complex mixtures through the use of a cation exchange medium.

34 Claims, 3 Drawing Sheets

(56) References Cited

OTHER PUBLICATIONS

Gaza-Bulseco et al., Characterization of the glycosylation state of a recombinant monoclonal antibody using weak cation exchange chromatography and mass spectrometry. J Chromatogr B Analyt Technol Biomed Life Sci. Feb. 1, 2008;862(1-2):155-60. doi: 10.1016/j.jchromb.2007.12.001. Epub Dec. 8, 2007.

Gilar, M., et al., "Mixed-mode Chromatography for Fractionation of Peptides, Phosphopeptides, and Sialylated Glycopeptides," Journal of Chromatography. A 1191(1-2):162-170, Elsevier, Netherlands (2008).

Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

Houel, S., et al., "N- and O-glycosylation Analysis of Etanercept Using Liquid Chromatography and Quadrupole Time-of-flight Mass Spectrometry Equipped With Electron-transfer Dissociation Functionality," Analytical Chemistry 86(1):576-584, American Chemical Society, United States (2014).

Langner, K-D., et al., "Synthesis of Biologically Active Deletion Mutants of Human Factor VIII:C," Behring Institute Mitteilungen 82:16-25, Behringwerke AG, Germany (1988). Abstract.

Lewandrowski, U., et al., "Enhanced N-glycosylation Site Analysis of Sialoglycopeptides by Strong Cation Exchange Prefractionation Applied to Platelet Plasma Membranes," Molecular & Cellular Proteomics 6(11 ): 1933-1941, American Society for Biochemistry and Molecular Biology, United States (2007).

Lyubarskaya et al., Analysis of recombinant monoclonal antibody isoforms by electrospray ionization mass spectrometry as a strategy for streamlining characterization of recombinant monoclonal antibody charge heterogeneity. Anal Biochem. Jan. 1, 2006;348(1):24-39. Epub Oct. 25, 2005.

Madhusudan, S., et al., "Study of Etanercept, a Tumor Necrosis Factor-Alpha Inhibitor, in Recurrent Ovarian Cancer," Journal of Clinical Oncology 23(25):5950-5959, American Society of Clinical Oncology, United States (2005).

Meulien, P., et al., "A New Recombinant Procoagulant Protein Derived from the cDNA Encoding Human Factor VIII," Protein Engineering 2( 4):301-306, IRL Press Ltd., England (I 988).

Millward et al., Effect of constant and variable domain glycosylation on pharmacokinetics of therapeutic antibodies in mice. Biologicals. Jan. 2008;36(1):41-7. Epub Sep. 24, 2007.

Santora et al., Characterization of maleuric acid derivatives on transgenic human monoclonal antibody due to post-secretional modifications in goat milk. Biomed Chromatogr. Sep. 2006;20(9):843-56.

Santora et al., Characterization of recombinant human monoclonal tissue necrosis factor-alpha antibody using cation-exchange HPLC and capillary isoelectric focusing. Anal Biochem. Nov. 1, 1999;275(1):98-108.

Sarrats et al., Glycan characterization of PSA 2-DE subforms from serum and seminal plasma. OMICS. Aug. 2010;14(4):465-74. doi: 10.1089/omi.2010.0050.

Sarver, N., et al., "Stable Expression of Recombinant Factor VIII Molecules Using a Bovine Papillomavirus Vector," DNA 6(6):553-564, Mary Ann Liebert, Inc., United States (1987).

Schiestl, M., et al., "Acceptable Changes in Quality Attributes of Glycosylated Biopharmaceuticals," Nature Biotechnology 29(4):310-312, Nature America, Inc., United States (2011).

Sheng, Q., et al., "A Novel Ionic-bonded Cellulose Stationary Phase for Saccharide Separation," Journal of Chromatography. A 1291:56-63, Elsevier, Netherlands (2013).

Staby et al., Comparison of chromatographic ion-exchange resins V. Strong and weak cation-exchange resins. J Chromatogr A. Jun. 23, 2006;1118(2):168-79. Epub May 5, 2006.

Stein et al., Cation exchange chromatography in antibody purification: pH screening for optimised binding and HCP removal. J Chromatogr B Analyt Technol Biomed Life Sci. Mar. 15, 2007;848(1):151-8. Epub Nov. 17, 2006.

Takegawa et al., Simple separation of isomeric sialylated N-glycopeptides by a zwitterionic type of hydrophilic interaction chromatography. J Sep Sci. Nov. 2006;29(16):2533-40.

Toole, J.J., et al., "A Large Region (approximately equal to 95 kDa) of Human Factor VIII is Dispensable for in vitro Procoagulant Activity," Proceedings of the National Academy of Sciences USA 83(16):5939-5942, National Academy of Sciences, United States (1986).

Tuytten, R., et al., "Application of a Combined Weak Cation-exchange/crown Ether Column: First Demonstrations of a Versatile Tool for Proteome Subselection," Analytical Chemistry 81(7):2456-2469, American Chemical Society, United States (2009).

Vermeer, C., "Gamma-carboxyglutamate-containing Proteins and the Vitamin K-dependent Carboxylase," The Biochemical Journal 266(3):625-636, Portland Press on behalf of the Biochemical Society, England (1990).

Zalevsky, J., et al., "Dominant-negative Inhibitors of Soluble TNF Attenuate Experimental Arthritis without Suppressing Innate Immunity to Infection," Journal of Immunology 179(3):1872-1883, American Association of Immunologists, United States (2007).

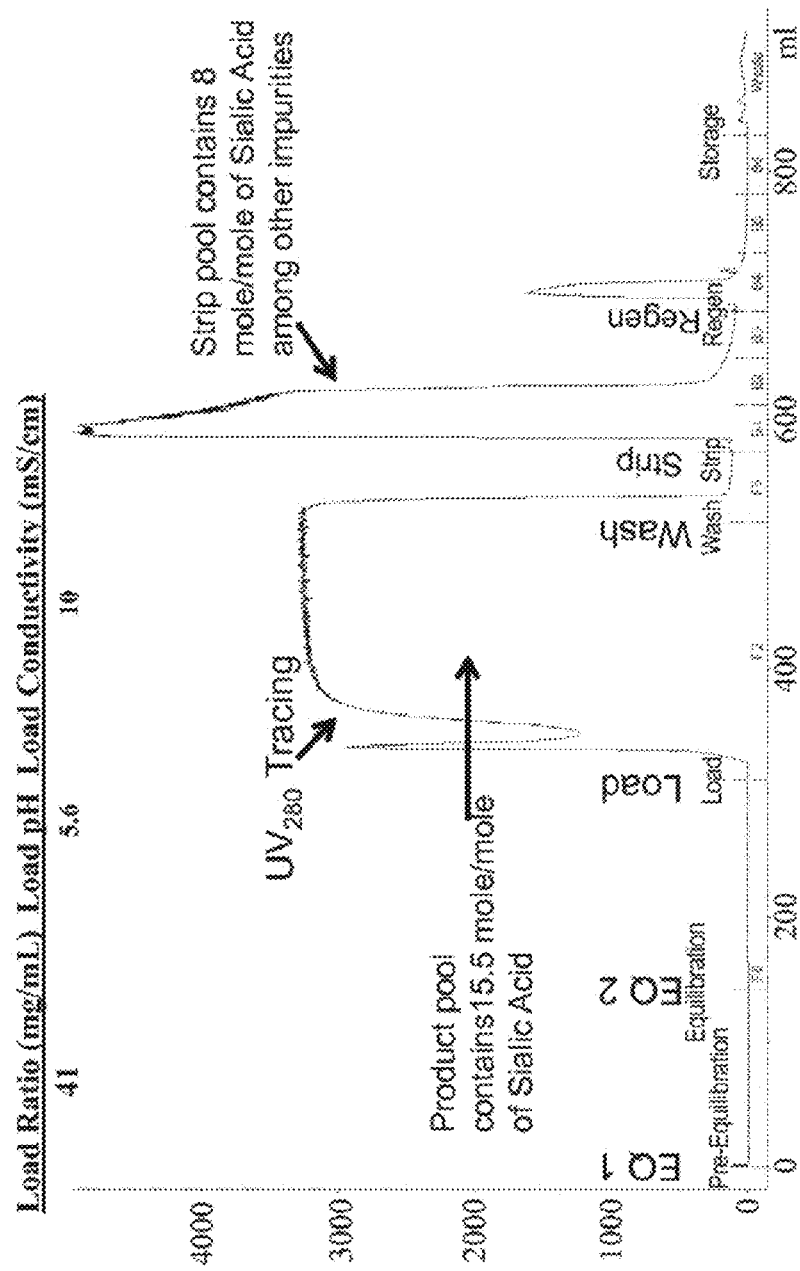
Figure 1: SE Hicap chromatogram

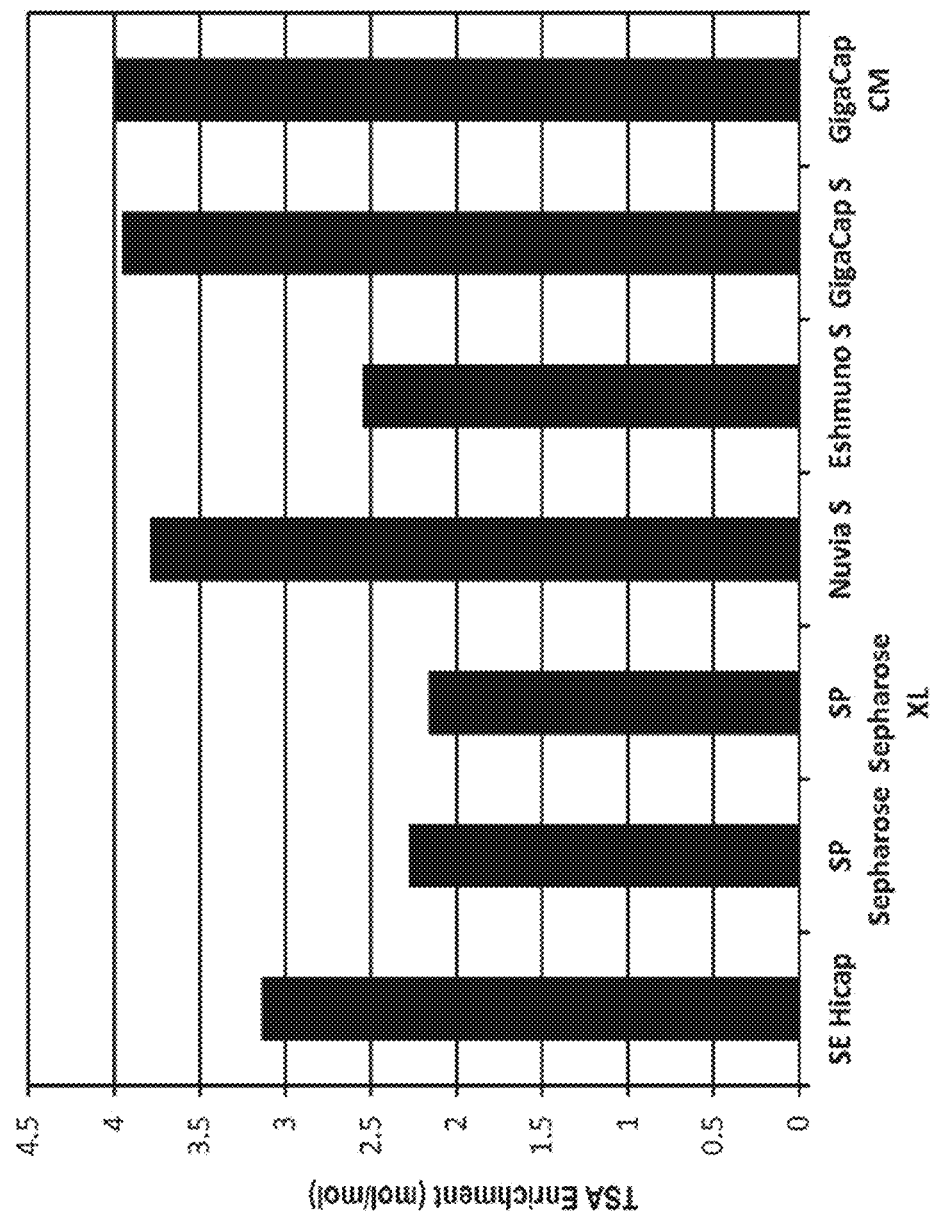
Figure 2: TSA enrichment by CEX resins

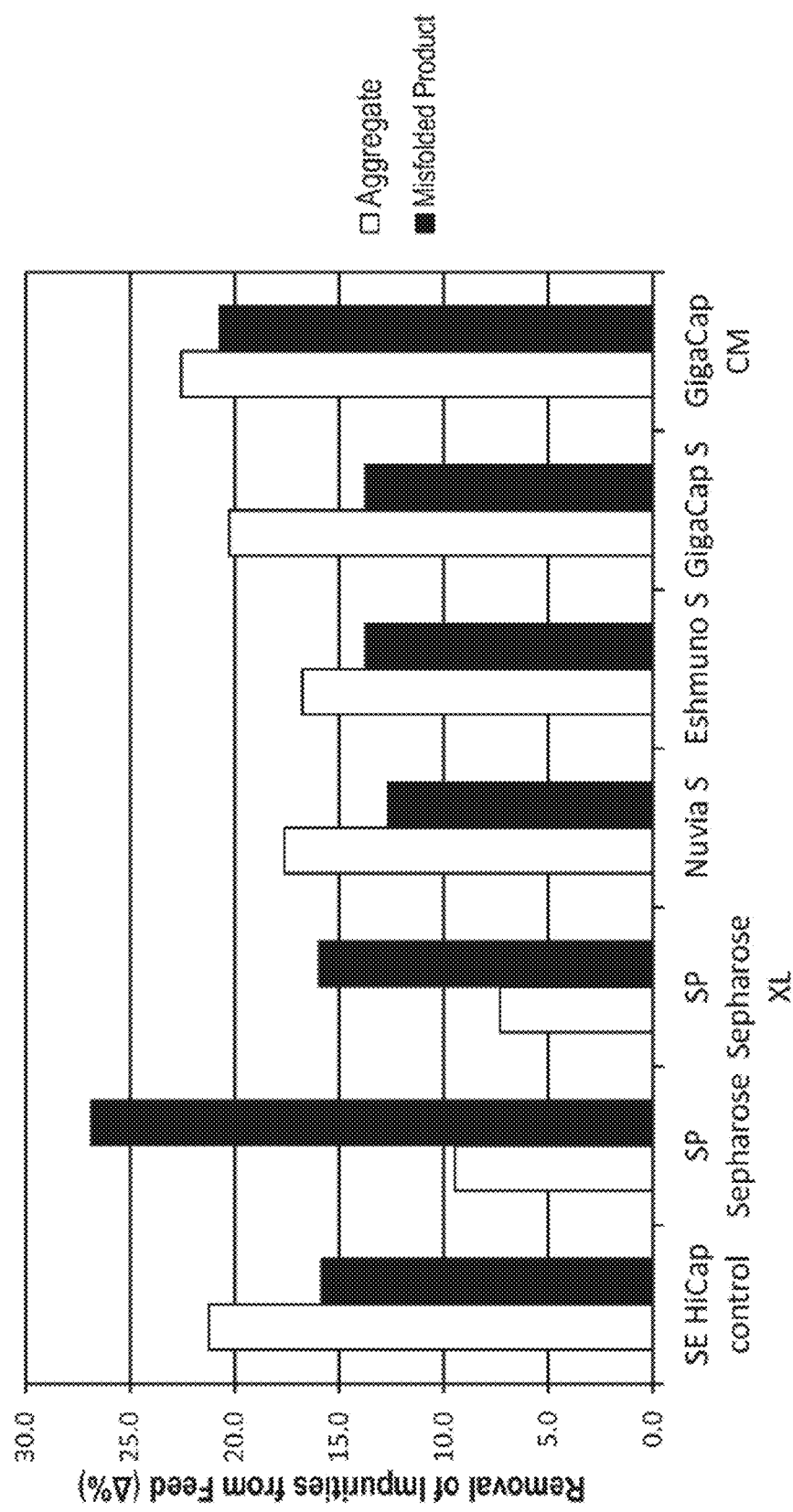
Figure 3: Removal of impurities by CEX resins

USE OF CATION-EXCHANGE CHROMATOGRAPHY IN THE FLOW-THROUGH MODE TO ENRICH POST-TRANSLATIONAL MODIFICATIONS

CROSS-REFERENCE TO RELATED APPLICATIONS

This Application is a Continuation of U.S. application Ser. No. 15/116,456, filed Aug. 3, 2016, entitled "USE OF CATION-EXCHANGE CHROMATOGRAPHY IN THE FLOW-THROUGH MODE TO ENRICH POST-TRANSLATIONAL MODIFICATIONS", which is a national stage filing under 35 U.S.C. 371 of International Patent Application Serial No. PCT/US2015/014469, filed Feb. 4, 2015, entitled "USE OF CATION-EXCHANGE CHROMATOGRAPHY IN THE FLOW-THROUGH MODE TO ENRICH POST-TRANSLATIONAL MODIFICATIONS", which claims the benefit of provisional U.S. Application Ser. No. 61/935,728, filed Feb. 4, 2014, entitled "USE OF CATION-EXCHANGE CHROMATOGRAPHY IN THE FLOW-THROUGH MODE TO ENRICH POST-TRANSLATIONAL MODIFICATIONS", the contents of each of which are incorporated herein by reference in their entireties.

BACKGROUND OF THE INVENTION

Specific post-translational modifications and impurity levels are often mandated by regulatory agencies for recombinant polypeptides intended for human administration. Often the level of post-translational modifications of recombinant polypeptides produced in cell lines in vitro differs from the level of post-translational modifications required for recombinant polypeptides intended for human administration. The glycosylation profile of a polypeptide can be affected by multiple factors including the type of production cell line, the growth conditions and the polypeptide sequence. Shiestl, M., et al. Nature Biotechnology 29(4):310 (2011).

There is a need in the art for methods that provide for enrichment of recombinant polypeptides with specific levels of particular post-translational modifications on a scale that is amenable for manufacturing processes, i.e. that maintains an acceptable product recovery and yield.

SUMMARY OF THE INVENTION

The present invention provides a method for enriching the level of post-translational modification of recombinant polypeptides, comprising: contacting a composition which comprises an initial population of recombinant polypeptides having different levels of post-translational modification with a cation exchange chromatography (CEX) medium operated in a flow-through mode; wherein recombinant polypeptides that do not bind the CEX medium are separated from recombinant polypeptides that bind the CEX medium, and wherein the recombinant polypeptides that do not bind the CEX medium comprise a higher level of post-translational modification compared to the bound recombinant polypeptides.

The present invention provide a method for enriching the level of post-translational modification of recombinant polypeptides, comprising:
 a) contacting a composition which comprises an initial population of recombinant polypeptides having different levels of post-translational modification with a cation exchange chromatography (CEX) medium operated in a flow-through mode; and
 b) separating recombinant polypeptides that do not bind the CEX medium from recombinant polypeptides that bind the CEX medium;
wherein the recombinant polypeptides that do not bind the CEX medium that are recovered comprise a higher level of post-translational modification compared to the bound recombinant polypeptides.

The present invention provides a method for enriching the level of post-translational modification of recombinant polypeptides, comprising:
 a) contacting a composition which comprises an initial population of recombinant polypeptides having different levels of post-translational modification with a cation exchange chromatography (CEX) medium operated in a flow-through mode;
 b) separating recombinant polypeptides that do not bind the CEX medium from recombinant polypeptides that bind the CEX medium; and
 c) recovering the recombinant polypeptides that do not bind the CEX medium;
wherein the recombinant polypeptides that do not bind the CEX medium comprise a higher level of post-translational modification compared to the bound recombinant polypeptides.

The present invention provides a method for enriching the level of post-translational modification of recombinant polypeptides, comprising:
 a) providing a composition which comprises an initial population of recombinant polypeptides having different levels of post-translational modification;
 b) contacting the composition with a cation exchange chromatography (CEX) medium operated in a flow-through mode;
 c) separating recombinant polypeptides that do not bind the CEX medium from recombinant polypeptides that bind the CEX medium; and
 d) recovering the recombinant polypeptides that do not bind the CEX medium;
wherein the recombinant polypeptides that do not bind the CEX medium comprise a higher level of post-translational modification compared to the bound recombinant polypeptides.

In some embodiments, the method further provides recovering the recombinant polypeptides that do not bind the CEX medium.

In some embodiments, the post-translational modification is sialylation or gamma-carboxyglutamate (Gla) formation. In some embodiments, the post-translational modification is sialylation.

In some embodiments, the total sialic acid content of the recombinant polypeptides that do not bind the CEX medium is between about 0.5 and about 6 moles of sialic acid per mole of protein higher than that of the initial population of recombinant polypeptides. In some embodiments, the total sialic acid content of the recombinant polypeptides that do not bind the CEX medium is between about 0.5 and about 4 moles of sialic acid per mole of protein higher than that of the initial population of recombinant polypeptides. In some embodiments, the total sialic acid content of the recombinant polypeptides that do not bind the CEX medium is between about 5% and about 100% higher than that of the initial population of recombinant polypeptides. In some embodiments, the total sialic acid content of the recombinant polypeptides that do not bind the CEX medium is between about 5% and about 40% higher than that of the initial population of recombinant polypeptides. In some embodiments, the total sialic acid content of the recombinant polypeptides that do not bind the CEX medium is between about 12 and about 20 moles of sialic acid per mole of protein. In some embodiments, the total sialic acid content of the recombinant polypeptides that do not bind the CEX medium is between about 14 and about 17 moles of sialic acid per mole of protein.

In some embodiments, the total sialic acid content of the initial population of recombinant polypeptides is about 10 to about 14 moles of sialic acid per mole of protein. In some embodiments, the total sialic acid content of the initial population of recombinant polypeptides is about 13-14 moles of sialic acid per mole of protein.

In some embodiments, the recombinant polypeptide comprises an Fe domain. In some embodiments, the recombinant polypeptide comprises an antibody.

In some embodiments, the recombinant polypeptide comprises an Fe fusion polypeptide comprising a ligand binding domain of a receptor. In a specific embodiment, the receptor is a TNF receptor. In a more specific embodiment, the recombinant polypeptide is etanercept.

In some embodiments, the recombinant polypeptide comprises a clotting factor. In some embodiments, the recombinant polypeptide is a monomer-dimer hybrid. Examples of clotting factors include Factor VII (FVII), FVIIa, Factor VIII (FVIII), Factor IX (FIX), or FIXa (FIX). FVIII can be full-length FVIII or B-domain deleted FVIII. FVIII can be single chain FVIII or dual chain FVIII.

In some embodiments, the contacting occurs at a load ratio between about 30 and about 100 mg total protein/ml CEX medium. In some embodiments, the contacting occurs at a load ratio between about 33 and about 54 mg total protein/ml CEX medium. In some embodiments, the contacting occurs at a load ratio of at least about 41 mg total protein/ml CEX medium.

In some embodiments, the contacting occurs at a pH between about 4 and about 7. In some embodiments, the contacting occurs at a pH between about 5 and about 6. In some embodiments, the contacting occurs at a pH between about 5.5 and about 5.8 In some embodiments, the contacting occurs at a pH of at least about 5.6.

In some embodiments, the contacting occurs at a conductivity between about 8 and about 12 mS/cm. In some embodiments, the contacting occurs at a conductivity of between about 9.5 and about 11 mS/cm. In some embodiments, the contacting occurs at a conductivity of at least about 10 mS/cm.

In some embodiments, the recombinant polypeptides that do not bind the CEX medium comprise about 25% to about 80% of the initial population of recombinant polypeptides. In some embodiments, the recombinant polypeptides that do not bind the CEX medium comprise about 55% to about 80% of the initial population of recombinant polypeptides.

In some embodiments, the CEX medium comprises one of the following ligands: sulfoethyl; sulphopropyl; sulfopropyl; $CH_2$—$SO_3^-$; $CH_2CH_2CH_2SO_3^-$; $SO_3^-$; or $CH_2$—COO. In some embodiments, the CEX medium comprises a sulfoethyl ligand.

In some embodiments, the CEX medium comprises a binding capacity of between about 120 and about 160 mg lysozyme/ml resin.

In some embodiments, the recombinant polypeptide is produced by a eukaryotic host cell. In specific embodiments, the eukaryotic host cell is a mammalian host cell.

In some embodiments, the contacting is performed at a manufacturing scale.

In some embodiments, the composition further comprises at least one impurity. Examples of impurities include a DNA, RNA, lipid or protein. In some embodiments, the impurity comprises a protein. Examples of the protein impurities include a truncated form of the recombinant polypeptide, an aggregated form of the recombinant polypeptide, or a misfolded form of the recombinant polypeptide.

In some embodiments, the method provides a final composition comprising the recombinant polypeptides that do not bind the CEX medium, wherein the final composition comprises less impurities than the composition that comprised the initial population of polypeptides.

BRIEF DESCRIPTIONS OF THE DRAWINGS

FIG. 1 illustrates a SE Hicap Chromatogram for the enrichment of sialylated etanercept. The load ratio was 31 mg/ml, the load pH was 5.6, and the load conductivity was 10 mS/cm. The product yield was 67%, and the total sialic acid of the product was 15 moles of sialic acid/mole of protein. Peak 1 is composed of clipped etanercept. Peak 2 is composed of native etanercept. Peak 3 is composed of misfolded etanercept.

FIG. 2 illustrates a comparison of the TSA enrichment of etanercept by various CEX resins (SE Hicap, SP Sepharose, SP Sepharose XL, Nuvia S, Eshmuno, GigaCap S, and GigaCap CM). The results were normalized to 50% product yield.

FIG. 3 illustrates a comparison of the impurities removed from a composition comprising etanercept by various CEX resins (SE Hicap, SP Sepharose, SP Sepharose XL, Nuvia S, Eshmuno, GigaCap S, and GigaCap CM). The results were normalized to 50% product yield.

DETAILED DESCRIPTION OF THE INVENTION

The present invention is directed to methods of enriching the level of post-translational modifications of recombinant polypeptides through the use of a chromatography medium. In preferred embodiments, the chromatography medium is an ion exchange chromatography medium utilized in a flow-through mode of operation.

In order to provide a clear understanding of the specification and claims, the following definitions are provided below.

Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd. ed., 2002, CRC Press; The Dictionary of Cell and Molecular Biology, 3rd ed., 1999, Academic Press; and the Oxford Dictionary Of Biochemistry And Molecular Biology Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "protein" or "polypeptide" refers to a polymer of two or more of the natural amino acids or non-natural amino acids.

Polypeptides may be either monomers or multimers. For example, in one embodiment, a protein of the invention is a dimer. A dimeric polypeptide of the invention may comprise two polypeptide chains or may consist of one polypeptide chain (e.g., in the case of a scFc molecule). In one embodiment, the dimers of the invention are homodimers, comprising two identical monomeric subunits or polypeptides (e.g., two identical Fc moieties or two identical biologically active moieties). In another embodiment, the dimers of the invention are heterodimers, comprising two non-identical monomeric subunits or polypeptides (e.g., comprising two different clotting factors or portions thereof or one cloning factor only). See, e.g., U.S. Pat. No. 7,404,956, incorporated herein by reference in its entirety.

"Recombinantly expressed polypeptide" and "recombinant polypeptide" refer to a polypeptide expressed from a host cell that has been genetically engineered to express that polypeptide. The recombinantly expressed polypeptide can be identical or similar to polypeptides that are normally expressed in the mammalian host cell. The recombinantly expressed polypeptide can also foreign to the host cell, i.e. heterologous to peptides normally expressed in the mammalian host cell. Alternatively, the recombinantly expressed polypeptide can be chimeric in that portions of the polypeptide contain amino acid sequences that are identical or similar to polypeptides normally expressed in the mammalian host cell, while other portions are foreign to the host cell. Any polypeptide that is expressible in a host cell may be produced in accordance with the present invention. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring. Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, etc.

Polypeptides that are "variants" of another peptide may have one or more mutations relative to the starting polypeptide, e.g., one or more amino acid residues which have been substituted with another amino acid residue or which has one or more amino acid residue insertions or deletions. In one embodiment, the polypeptide comprises an amino acid sequence which is not naturally occurring. Such variants necessarily have less than 100% sequence identity or similarity with the starting polypeptide. In another embodiment, the variant will have an amino acid sequence from about 75% to less than 100% amino acid sequence identity or similarity with the amino acid sequence of the starting polypeptide, for example, from about 80% to less than 100%, from about 85% to less than 100%, from about 90% to less than 100% (e.g., 92%, 93%, 94%, 95%, 96%, 97%, 98%, 99%) and from about 95% to less than 100%, e.g., over the length of the variant molecule. In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

The term "aggregates", as used herein, refers to polypeptide aggregates. It encompasses multimers (such as dimers, tetramers or higher order aggregates) of the recombinant polypeptide to be purified and may result, e.g., in high molecular weight aggregates.

The term "chromatography" refers to any kind of technique which separates a recombinant polypeptide of interest from other molecules present in a mixture. Usually the recombinant polypeptide of interest is separated from other molecules as a result of differences in binding affinity.

The term "binding" a molecule to a chromatography resin means exposing the molecule to chromatography resin under appropriate conditions (e.g. pH/conductivity) such that the molecule is reversibly immobilized in or on the chromatography resin by virtue of ligand-protein interactions. Non-limiting examples include ionic interactions between the molecule and a charged group or charged groups of the ion exchange material and an immunoglobulin.

The terms "flow-through," "flow-through process," "flow-through mode," and "flow-through chromatography," as used interchangeably herein, refer to a product separation technique in which at least one product (e.g., a recombinant polypeptide with specific post-translational modifications) contained in a sample is intended to flow-through a chromatographic resin or media, while at least one potential contaminant or impurity binds to the chromatographic resin or media.

The terms "chromatography resin", "chromatography media" and "chromatography medium" are used interchangeably and refer to any kind of solid phase which separates a recombinant polypeptide of interest from other molecules present in a mixture. Usually, the recombinant polypeptide of interest is separated from other molecules as a result of differences in binding affinity between the other molecules in the mixture and the recombinant polypeptide of interest. use of any known, or subsequently disclosed or developed, chromatography media or matrix. Examples, without limitation, of such media comprise; ion exchange media; anion exchange media; cation exchange media; hydroxyapatite media; hydrophobic interaction chromatography media; antibody-affinity media (e.g., Protein-A or variants thereof); immunoglobulin Fc-region affinity media (e.g., Fc-receptor affinity media); and, ligand-affinity media; receptor-affinity media; and mixed-mode media.

As used herein the terms "ion-exchange" and "ion-exchange chromatography" are used to refer to a chromatographic process in which a recombinant polypeptide of interest interacts or does not interact with charged compound linked (such by covalent attachment) to a solid phase ion exchange material such that the recombinant polypeptide of interest interacts non-specifically with the charged compound more or less than other recombinant polypeptides or impurities in the mixture. The contaminant in the mixture elutes from a column of the ion exchange material faster or slower than the recombinant polypeptide of interest or are bound to or excluded from the resin relative to the recombinant polypeptide of interest. "Ion-exchange chromatography" specifically includes cation exchange, anion exchange, and mixed mode ion exchange chromatography.

The "pI" or "isoelectric point" of a polypeptide refer to the pH at which the polypeptide's positive charge balances its negative charge, pI can be calculated from the net charge of the amino acid residues or sialic acid residues of attached carbohydrates of the polypeptide or can be determined by isoelectric focusing.

The phrase "ion exchange material" refers to a solid phase that is negatively charged (i.e., a cation exchange resin) or positively charged (i.e., an anion exchange resin). The charge may be provided by attaching one or more charged ligands to the solid phase, e.g., by covalent linking. Alternatively, or in addition, the charge may be an inherent property of the solid phase (e.g., as is the case for silica, which has an overall negative charge).

The phrase "anion exchange resin" or "AEX" refers to a solid phase which is positively charged, e.g., having one or more positively charged ligands, such as quaternary amino groups, attached thereto. Commercially available anion exchange resins include DEAE cellulose, QAE SEPHADEX™ and FAST Q SEPHAROSE™ (Pharmacia). Anion exchange chromatography can bind the target molecule (e.g., an Fc region containing target protein) followed by elution or can predominately bind the impurities while the target molecule "flows through" the column.

The phrase "cation exchange resin" or "CEX" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. For example, cation exchange chromatography can be performed under conditions in which the resin bind the target molecule (e.g. an Fc region containing target protein) followed by elution (cation exchange bind and elution chromatography or "CIEX"). Alternatively, CEX can be run in a mode which it predominately binds the impurities while the target molecule "flows through" the column (cation exchange flow-through chromatography). Commercially available CEX resins include Fractogel SE Hicap, GE SPXL, GE SP Sepharose, Millipore Eshmuno S, Tosoh Gigacap CM, Tosoh Gigacap S-650, BioRad Nuvia S. The phrase "cation exchange resin" or "CEX" also refers to a mixed-mode resin that is partially or entirely operated in cation-exchange mode of chromatography. Commercially available mixed-mode resins include Capto MMC. The purification method disclosed herein utilizes a cation exchange chromatography step which is performed in a flow-through mode.

Chromatography Methods

The present invention utilizes a "flow-through" mode of operation wherein a recombinant polypeptide is allowed to contact a chromatography medium (or other matrix). During the contacting, a recombinant polypeptide having a selected characteristic (such as a particular post-translational modification) preferentially does not bind to the chromatography medium (or other matrix) while recombinant polypeptides (as well as other impurities) not having the selected characteristic, or having less of the selected characteristic (such as a recombinant polypeptide having a lower overall net negative charge or a lower sialic acid content) binds to the medium (or matrix). The flow-through, containing the enriched recombinant polypeptide, is recovered. The recombinant polypeptide mixture obtained is enriched with a higher concentration of product having the selected (target) characteristic compared to the composition containing the initial population of recombinant polypeptides prior to contacting with the chromatography medium.

In some embodiments, the present invention is directed to selectively enriching recombinant polypeptides wherein the selected or desired product characteristic is that of having increased or enhanced overall (total) levels of sialic acid content. In some embodiments, a recombinant polypeptide with increased total sialic acid content is obtained by contacting a composition that contains a population of exchange chromatography medium (e.g., SE Hicap) with a mixture of the recombinant polypeptide. Undesired products (e.g., product with a lower sialic acid content, and other impurities) are allowed to bind the chromatography medium, then the selected product (with high sialic acid content) flows through the column and is recovered.

Methods of the present invention can be adapted and applied to the separation/purification of recombinant polypeptides based on any another of physical, biological, and/or chemical characteristics. For example, product isoforms may be selectively separated on the basis of charge and/or hydrophobicity by using appropriate adsorbents (such as, for example, strong or weak cation exchange resins for charge based separations and hydrophobic adsorbents for separations based on hydrophobicity). Additionally, methods of the invention may be applied using mixed-mode chromatography (mixed-mode media) for separations based on two orthogonal product attributes (e.g., charge and hydrophobicity).

In some embodiments, the invention relates to a method for enriching, increasing, enhancing, or augmenting the level of post-translational modification of recombinant polypeptides comprising: contacting a composition which comprises an initial population of recombinant polypeptides having different levels of post-translational modification with a cation exchange chromatography (CEX) medium operated in a flow-through mode; wherein recombinant polypeptides that do not bind the CEX medium are separated from recombinant polypeptides that bind the CEX medium, and wherein the recombinant polypeptides that do not bind the CEX medium comprise a higher or increased level of post-translational modification compared to the bound recombinant polypeptides.

In some embodiments, the recombinant polypeptides that do not bind the CEX medium are more negatively charged than the polypeptides or other impurities that bind the CEX resin. In some embodiments, the invention further comprises recovering the recombinant polypeptides that do not bind the CEX medium.

In some embodiments, recombinant polypeptides with higher levels of specific post-translational modifications are separated from recombinant polypeptides with lower levels of post-translational modifications through the use of a CEX medium operated in flow-through mode. "Separating" refers to increasing the degree of purity of a recombinant polypeptide of interest from a composition or sample comprising the polypeptide and one or more impurities or contaminants. In some embodiments, the recombinant polypeptide of interest is separated from the other polypeptides or impurities in the composition through the use of charge. In some embodiments, the recombinant polypeptide of interest is more negatively charged than other polypeptides or impurities in the composition such that the recombinant polypeptide of interest does not bind to the CEX medium operated in flow-through mode. In some embodiments, the degree of purity of the recombinant polypeptide of interest is increased by removing (completely or partially) at least one impurity from the composition. In some embodiments, the post-translational modification is sialylation or gamma-carboxyglutamate (Gla) formation.

In some embodiments, the post-translational modification is sialylation. Sialylation is the final step of human glycosylation. Total sialic residue refers to the total number of sialic residues on a given recombinant polypeptide. The sialylation of a protein is critical to protein function, as the in vivo biological activity of glycosylated proteins is known to be dependent on the number of sialic acid units per molecule. Shiestl, M., et al. Nature Biotechnology 29(4):310 (2011). The loss of sialic acid frequency leads to reduced glycoprotein solubility and reduced circulatory half-life. As a result the purification and therapeutic effectiveness of a recombinant polypeptide is dependent on the sialic acid content. The glycosylation profile of a polypeptide can be affected by many factors including the type of production cell line, the growth conditions, and the polypeptide sequence. Shiestl, M., et al. Nature Biotechnology 29(4):310 (2011).

In some embodiments, the total sialic acid content of the recombinant polypeptide is between about 0.5 and about 6, between about 1 and about 4, or between about 1 and about 3 moles of sialic per mole of protein higher than that of the initial population of recombinant polypeptides. In some embodiments, the total sialic acid content of the recombinant polypeptide is between about 0.6 and about 2.7 moles of sialic per mole of protein higher than that of the initial population of recombinant polypeptides. In some embodiments, the total sialic acid content of the recombinant proteins is at least about 0.5, at least about 1.0, at least about 1.5, at least about 2.0, at least about 2.5, at least about 3.0, at least about 3.5, at least about 4.0, at least about 4.5, at least about 5.0, at least about 5.5, or at least about 6.0 moles of sialic per mole of protein higher than that of the initial population of recombinant polypeptides.

In some embodiments, the total sialic content of the recombinant polypeptides that do not bind the CEX medium is between about 5% and about 100%, between about 5% and about 90%, between about 5% and about 80%, between about 5% and about 70%, between about 5% and about 60%, between about 5% and about 50%, and between about 5% and about 40% higher than that of the composition containing the initial population of recombinant polypeptides. In some embodiments, the total sialic content of the recombinant polypeptides that do not bind the CEX medium is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100% higher than that of the composition containing the initial population of recombinant polypeptides.

In some embodiments, the total sialic acid content of the recombinant polypeptides that do not bind the CEX medium is between about 13 and about 20, between about 13.5 and about 19, between about 14 and about 18, between about 14 and about 17, or between about 14 and about 16.5 moles of sialic acid per mole of protein. In some embodiments, the total sialic acid content of the recombinant polypeptides that do not bind the CEX medium is between about 14.1 and about 16.2.

In some embodiments, the total sialic content of the initial content of the initial population of recombinant polypeptides is between about 10 and about 14, between about 10.5 and about 14, between about 11 and about 14, between about 11.5 and about 14, between about 12 and about 14, between about 12.5 and about 14, or between about 13 and about 14 moles of sialic acid per mole of protein. In some embodiments, the total sialic acid content of the initial population of recombinant polypeptides is at least about 10, at least about 10.5, at least about 11, at least about 11.5, at least about 12, at least about 12.5, at least about 13, at least about 13.5 or at least about 14 moles of sialic acid per mole of protein. In some embodiments, the total sialic acid, content of the initial population of recombinant polypeptides is at least about 13.5 moles of sialic acid per mole of protein.

In some embodiments, the post-translational modification is gamma-carboxyglutamate (Gla) formation. The carboxylation/gamma-carboxyglutamic (GLA) domain is a Vitamin-K dependent domain. At the GLA domain, Vitamin K mediates the carboxylation of glutamate residues to form gamma-carboxyglutamate (Gla). Vermeer, C. *Biochem J.* 266: 625-636 (1990). Gla plays a key role in calcium binding and has been found to be critical for specific conformational transitions in clotting factor proteins. Freedman, S. J. et al., J. Biol. Chem. 271(27): 16227-36 (1996).

In some embodiments, the Gla content of the recombinant polypeptides that do not bind the CEX medium is between about 5% and about 100%, between about 5% and about 90%, between about 5% and about 80%, between about 5% and about between about 5% and about 60%, between about 5% and about 50%, and between about 5% and about 40% higher than that of the initial population of recombinant polypeptides.

In some embodiments, the total Gla content of the recombinant polypeptides that do not bind the CEX medium is between about 5% and about 100%, between about 5% and about 90%, between about 5% and about 80%, between about 5% and about 70%, between about 5% and about 60%, between about 5% and about 50%, and between about 5% and about 40% higher than that of the initial population of recombinant polypeptides.

In some embodiments of the invention, a chromatography medium in "flow-through" mode of operation is utilized to enrich a composition of recombinant polypeptides having a specific post-translational modification.

The load ratio describes the total amount of the composition that is contacting the chromatography medium per volume of medium. If the load ratio is too high, then, in the case of a column run in flow-through mode, some impurities may not bind the medium. In some embodiments, the contacting of the composition with the medium occurs at a load ratio of at least about 30 mg total protein/ml CEX medium, at least about 35 mg total protein/ml CEX medium, at least about 40 mg total protein/ml CEX medium, at least about 45 mg total protein/ml CEX medium, at least about 50 mg total protein/ml CEX medium, at least about 55 mg total protein/ml CEX medium, at least about 60 mg total protein/ml CEX medium, at least about 70 mg total protein/ml CEX medium, at least about 80 mg total protein/ml CEX medium, at least about 90 mg total protein/ml CEX medium, at least about 100 mg total protein/ml CEX medium, at toast about 110 mg total protein/ml CEX medium, at least about 120 mg total protein/ml CEX medium, at least about 130 mg total protein/ml CEX medium, at least about 140 mg total protein/ml CEX medium, or at least about 150 mg total protein/ml CEX medium. In some embodiments, the contacting occurs at a load ratio of 41 mg total protein/ml CEX medium. In some embodiments, the contacting of the composition with the medium occurs at a load ratio of between about 30 mg total protein/ml CEX medium and about 150 mg total protein/ml CEX medium, between about 30 mg total protein/ml CEX medium and 125 mg total protein/ml CEX medium, between about 30 mg total protein/ml CEX medium and 100 mg total protein/ml CEX medium, between about 30 mg total protein/ml CEX medium and 73 mg total protein/ml CEX medium, between about 30 mg total protein/ml CEX medium and 60 mg total protein/ml CEX medium, or between about 33 mg total protein/ml CEX medium and 54 mg total protein/ml CEX medium.

The pH of the contacting step is critical because it determines which charged molecules will bind the column and which will not bind. In some embodiments, the contacting of the composition with the medium occurs at a pH of at least about 3, at least about 4, at least about 5, at least about 5.5, at least about 6, at least about 6.5, at least about 7, at least about 8 or at least about 9. In some embodiments, the contacting occurs at a pH of 5.6. In some embodiments, the contacting of the composition with the medium occurs at a pH between about 3 and about 9, between about 4 and about 8, between about 4 and about 7, between about 5 and about 7, between about 5 and about 6, or between about 5.5 and about 5.8.

The conductivity of the contacting step is critical because it determines which molecules will bind the column and which will not bind. In some embodiments, the contacting of the composition with the medium occurs at a conductivity of at least about 8 mS/cm, at least about 8.5 mS/cm, at least about 9 mS/cm, at least about 10 mS/cm, at least about 10.5 mS/cm, at least about 11 mS/cm, at least about 11.5 mS/cm, at least about 12 mS/cm, at least about 12.5 mS/cm, or at least about 13 mS/cm. In some embodiments the contacting occurs at a conductivity of 10 mS/cm. In some embodiments the contacting occurs at a conductivity of between about 8 mS/cm and about 12 mS/cm, between about 8.5 mS/cm and 11.5 mS/cm, between about 9 mS/cm and about 11.5 mS/cm, between about 9 mS/cm and about 11 mS/cm, or between about 9.5 mS/cm and 11 mS/cm.

In some embodiments, the chromatography medium is ion exchange media; anion exchange media; cation exchange media; hydroxyapatite media; hydrophobic interaction chromatography media; antibody-affinity media (e.g., Protein-A or variants thereof); immunoglobulin Fc-region affinity media (e.g., Fc-receptor affinity media); and, ligand-affinity media; receptor-affinity media; or mixed-mode media. In preferred embodiments, the chromatography medium is a CEX resin. Embodiments of the invention include use of any known, or subsequently disclosed or developed, CEX chromatography media or matrix. In some embodiments, the CEX resin is a Fractogel SE Hicap, GE SPXL, GE SP Sepharose, Millipore Eshmuno S, Tosoh Gigacap CM, Tosoh Gigacap S-650, BioRad Nuvia S, or Capto MMC. In some embodiments, the CEX medium comprises a ligand that is sulfoethyl; sulphopropyl; sulfopropyl; $CH_2$—$SO_3^-$; $CH_2CH_2CH_2SO_3^-$; $SO_3^-$; $CH_2$—$COO^-$; or a multimodal weak cation exchanger. In some embodiments, the CEX medium comprises a matrix that crosslinked polymethacrylate 6% crosslinked agarose with dextran surface extenders, agarose, surface grafted rigid polyvinyl ether hydrophilic polymer, or highly cross-linked agarose. In some embodiments, the CEX medium is any known matrix. In some embodiments, the CEX medium comprises a sulfoethyl ligand. In some embodiments, the CEX resin is Fractogel SE Hicap.

In some embodiments, the CEX medium comprises a binding capacity or ligand capacity of between about 100 and about 200 mg lysozyme/ml resin, between about 110 and 190 mg lysozyme/ml resin, between about 120 and about 180 mg lysozyme/ml resin, between about 120 and about 170 mg lysozyme/ml resin, between about 120 and about 160 mg lysozyme/ml resin, or between about 125 and 160 lysozyme/ml resin.

The ion exchange rate between the medium and the composition increases as the temperature increases. Temperature can also affect the selectivity of the column. In some embodiments, the temperature during the contacting of the composition with the medium is between about 16 and about 26° C., between about 18 and about 24° C., or between about 20 and about 23° C. In some embodiments, the temperature during the contacting of the composition with the medium is at least about 15° C., at least about 16° C., at least about 17° C., at least about 18° C., at least about 19° C., at least about 20° C., at least about 21° C., at least about 22° C., at least about 23° C., at least about 24° C., at least about 25° C., least about 26° C. or at least about 30° C. In some embodiments, the temperature during the contacting of the composition with the medium is about 22° C.

A higher flow rate decreases the process time, but a higher flow rate may decrease the efficiency of separation, due to decreased contacting time between the composition and the medium. In some embodiments, the process flow rate is between about 75 cm/hr and about 150 cm/hr, between about 100 cm/hr and about 150 cm/hr, or between about 120 cm/hr and about 150 cm/hr. In some embodiments, the process flow rate is at least about 75 cm/hr, at least about 80 cm/hr, at least about 90 cm/hr, at least about 100 cm/hr, at least about 110 cm/hr, at least about 115 cm/hr, at least about 120 cm/hr, at least about 125 cm/hr, at least about 130 cm/hr, at least about 135 cm/hr, at least about 140 cm/hr, or at least about 150 cm/hr. In some embodiments, the process flow rate is about 125 cm/hr.

Embodiments of the invention include methods for recovering a selected recombinant polypeptide at a manufacturing scale; including a method wherein the selected recombinant polypeptide is a therapeutically useful or beneficial compound.

In some embodiments the composition containing the initial population of recombinant polypeptides contains only the recombinant polypeptide of interest with differing levels of the selected characteristic. In some embodiments, the composition containing the initial population of recombinant polypeptides also contains additional polypeptides that have a different amino acid sequence than the recombinant polypeptide of interest. In some embodiments, the additional polypeptides are recombinant. In some embodiments, the composition containing the initial population of recombinant polypeptides also contains impurities. In some embodiments, the impurity is a DNA, RNA, lipid or protein molecule. In some embodiments, the impurity is a truncated form of the recombinant polypeptide, an aggregated form of the recombinant polypeptide, or a misfolded form of the recombinant polypeptide. In some embodiments, the composition containing the recombinant polypeptide that does not bind the CEX medium has less impurities that the composition that contained the initial population of recombinant polypeptide. In some embodiments, the composition containing the recombinant polypeptide that does not bind the CEX medium has at least about 5%, at least about 10%, at least about 25%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 95%, or at least about 99% less impurities than the composition that contained the initial population of recombinant polypeptides.

In some embodiments, the recombinant polypeptides that do not bind the CEX medium are between about 10% and about 90%, between about 20% and about 80%, between about 30% and about 80%, between about 40% and about 80%, between about 50% and about 80%, or between about 55% and about 80% of the recombinant polypeptides of the composition comprising the initial population. In some embodiments, the recombinant polypeptides that do not bind the CEX medium are between about 55% and about 80% of the recombinant polypeptides of the composition comprising the initial population.

In one embodiment, product may be selectively enriched/separated, for example, based on peak product pI values wherein, for example, higher pI isoforms may be separated from lower pI product isoforms on a cation exchange adsorbent.

In some embodiments, the recombinant polypeptides that do not bind the CEX medium are subjected to one or more further purification steps following, the CEX chromatography. In some embodiments, the composition containing the initial population of recombinant polypeptides is subjected to one or more purification steps prior to the contacting with the CEX medium. In some embodiments, the pH and the conductivity of the composition with the initial population of recombinant polypeptides are adjusted prior to contacting the composition with the CEX medium. In some embodiments the pH of the recombinant polypeptides that do not bind the CEX medium is adjusted following the contacting with the CEX medium.

Recombinant Polypeptides of the Invention

Embodiments of the invention are useful for obtaining highly homogeneous mixtures of a wide variety of recombinant polypeptides with specific levels of post-translational modifications. Some examples of such recombinant polypeptides include, without limitation, proteins and protein fragments (i.e., full-length and partial length polypeptides/peptides), antibodies (immunoglobulins), heterologous fusion proteins, etc. In some embodiments, the polypeptide is a dimer. In some embodiments, the polypeptide is a monomer.

In one embodiment, the recombinant polypeptide is a non-immunoglobulin proteins (or fragments thereof) fused with an immunoglobulin (or domains, regions, of fragments thereof). In some embodiments, the recombinant polypeptide comprises an Fc domain. In some embodiments, the recombinant polypeptide comprises an antibody. In one embodiment, for example, methods of the invention are used for separation/purification of a recombinant polypeptide comprising an extracellular receptor ligand-binding domain linked (i.e., "fused") with the Fc-region of an immunoglobulin (such as the Fc region of an IgG molecule). Examples of Fc-fusion proteins can be seen in Table 1.

TABLE 1

| Key Fc-fusion proteins and monoclonal antibodies (mAbs) in the clinic | | | | |
|---|---|---|---|---|
| Trade name (generic name) | Description | Indication of first FDA approval | Stage | Company |
| Fc-fusion | | | | |
| Nulojix (belatacept) | CTLA-4 fused to the Fc of human IgG1 | Organ rejection | FDA Approved (2011) | Bristol-Meyers Squibb |
| Eylea (aflibercept) | VEGFR1/VEGFR2 fused to the Fc of human IgG1 | Age related macular degeneration | FDA Approved (2011) | Regeneron Pharmaceuticals |
| Arcalyst (rilonacept) | IL-1R fused to the Fc of human IgG1 | Cryopyrin-associated periodic syndromes | FDA Approved (2008) | Regeneron Pharmaceuticals |
| NPlate (romiplostim) | Thrombopoietin-binding peptide fused to the Fc of human IgG1 | Thrombocytopenia in chronic immune thrombocytopenic purpura patients | FDA Approved (2008) | Amgen/Pfizer |

TABLE 1-continued

Key Fc-fusion proteins and monoclonal antibodies (mAbs) in the clinic

| Trade name (generic name) | Description | Indication of first FDA approval | Stage | Company |
|---|---|---|---|---|
| Orencia (abatacept) | Mutated CTLA-4 fused to the Fc of human IgG1 | Rheumatoid arthritis | FDA Approved (2005) | Bristol-Meyers Squib |
| Amevive (alefacept) | LFA-3 fused to the Fc of human IgG1 | Psoriasis and transplant rejection | FDA Approved (2003) | Astellas Pharma |
| Enbrel (etanercept) | TNFR fused to the Fc of human IgG1 | Rheumatoid arthritis | FDA Approved (1998) | Amgen/Pfizer | mAbs

| Trade name (generic name) | Description | Indication of first FDA approval | Stage | Company |
|---|---|---|---|---|
| Rituxan/MabThera (rituximab) | Chimeric mouse/human IgG1 targeting CD20 | B cell lymphomas | FDA Approved (2006) | Biogen Idec/Genentech Hoffman-La Roche (Europe) |
| Herceptin (trastuzumab) | Chimeric mouse/human IgG1 targeting HER2 | Breast cancer and gastroesophageal junction adenocarcinoma | FDA Approved (2006) | Genentech |
| Campath/Lemtrada (alemtuzumab) | Humanized IgG1 targeting CD52 on B and T lymphocytes | B cell chronic lymphocytic leukemia. In phase IIIa trials for multiple sclerosis | FDA Approved (2007) | Genzyme |
| Prolia/Xgeva (denosumab) | Fully human IgG2 targeting RANKL | Osteoporosis | FDA Approved (2010) | Amgen |
| Tysabri (natalizumab) | Humanized IgG4 tageting alpha-4 integrin | Multiple sclerosis and Crohn's disease | FDA Approved (2004) | Biogen Idec and Élan |
| Vectibix (panitumumab) | Fully human IgG2 targeting EGFR, ErbB-1 and HER1 | Metastatic colorectal cancer (in patients with non-mutated KRAS | FDA Approved (2006) | Amgen |
| Soliris (eculizumab) | Humanized IgG2/4κ targeting complement protein C5 | Paroxysmal nocturnal haemoglobinuria to reduce haemolysis | FDA Approved (2007) | Alexion Pharmaceuticals |
| Erbitux (cetuximab) | Chimeric mouse human IgG1 targeting EGFR, ErbB-1 and HER1 | Metastatic colorectal cancer (in patients with non-mutated KRAS | FDA Approved (2006) | Bristol-Myers Squibb and Eli Lilly |
| Avastin (bevacizumab) | Humanized IgG1 targeting VEGF | Metastatic colorectal cancer and HER2-negative metastatic breast cancer | FDA Approved (2008) Withdrawn (2011) | Genentech/Roche |
| Remicade (infliximab) | Chimeric mouse human IgG1 targeting TNF-α | Psoriasis, Crohn's disease, ankylosing spondylitis, rheumatoid arthritis | FDA Approved (1998) | Janssen Biotech/Schering-Plough |

In one embodiment, the recombinant polypeptide is an Fc fusion polypeptide comprising a ligand binding domain of a receptor. In some embodiments, the receptor is a Tumor necrosis factor ("TNF") receptor. In some embodiments, the recombinant polypeptide is etanercept. Etanercept is a dimeric recombinant therapeutic glycoprotein, which consisting of the extracellular ligand binding portion of the human 75 kilodalton human tumor necrosis factor receptor linked to the constant region (Fc) of human IgG1. The INF receptor region binds to soluble TNF-α found in the bloodstream, thereby reducing a variety of inflammatory responses, including many autoimmune diseases. Etanercept is as a TNF inhibitor, an acts as a decoy receptor that binds to TNF. Zalevsky, J. et al., *J. Immunol.* 179(3): 1872-83. Etanercept acts in a similar function to naturally occurring soluble TNF receptors. However, as etanercept is a fusion protein, it has a greater half-life in the bloodstream, and therefore has a longer impact than a naturally occurring receptor. Madhusudan, S. *J. Clin Oncol.* 23(25): 5950-9. The Fc portion of the fusion protein transiently anchors to Fc receptors expressed on the surface of endothelial cells, which delays the degradation and increases the half-life of etanercept.

Etanercept requires N-glycosylation for biological activity. Glycosylated proteins are complex molecules and even a well-controlled product may consist of several hundred or more glycoforms with different glycan compositions on the same amino acid sequence. The in vivo biological activity of glycosylated proteins is known to be dependent on the number of sialic acid units per molecule, which is a result of the available sialylation sites, the antenniarity of the N-glycans and the completeness of sialylation. Shiestl, M., et al. *Nature Biotechnology* 29(4):310 (2011).

In some embodiments, the recombinant polypeptide comprises a clotting factor. In some embodiments, the clotting factor is selected from Factor VII (FVII), FVIIa, Factor VIII (FVIII), Factor IX (FIX), or FIXa (FIX). In some embodiments, the FVIII is full-length FVIII or B-domain deleted FVIII. In some embodiments, the FVIII is single chain FVIII or dual chain FVIII.

In some embodiments, the recombinant polypeptide is a monomer-dimer hybrid. A monomer-dimer hybrid is a chimeric protein having a dimeric aspect and a monomeric aspect, wherein the dimeric aspect relates to the fact that it is comprised of two polypeptide chains each comprised of a portion of an immunoglobulin constant region, and wherein the monomeric aspect relates to the fact that only one of the two chains is comprised of a therapeutic biologically active molecule. Monomer-dimer hybrids are described in detail is U.S. Pat. No. 7,404,956, which is incorporated herein by reference in its entirety.

"Factor VII" "FVII" refers to a coagulation factor protein synthesized in the liver and secreted into the blood as a single chain zymogen with a molecular weight of approximately 50 kDa. The FVII zymogen is converted into an activated form (FVIIa) by proteolytic cleavage. FVII is disclosed in U.S. Publ. No. 2011/0046061 and Int'l Publ. No. PCT/US2013/44842, each of which is incorporated herein by reference in its entirety.

"Factor VIII" or "FVIII" refers to a blood coagulation factor protein and species and sequence variants thereof that includes, but is not limited to, the 2351 amino acid single-chain precursor protein (with a 19-amino acid hydrophobic signal peptide), the mature 2332 amino acid factor VIII protein of approximately 270-330 kDa with the domain structure A1-A2-B-A3-C1-C2, as well as the circulating heterodimer of two chains that form as a result of proteolytic cleavage after R1648 of a heavy chain form composed of A1-A2-B (in the range of 90-220 kD) of amino acids 1-1648 (numbered relative to the mature FVIII form) and a light chain A3-C1-C2 of 80 kDa of amino acids 1649-2232, each of which is depicted schematically in FIG. 1. "Factor VIII" or "FVIII" also can be sequence variants that retain at least a portion of the biological activity of the native circulating protein, including truncated sequences, a sequence that includes heterologous amino acids, or a single chain FVIII (scFVIII) in which the heavy and light chains are covalently connected by a linker. As used herein, "FVIII" shall be any functional form of factor VIII molecule with the typical characteristics of blood coagulation factor VIII capable of in vivo or in vitro correction of human factor VIII deficiencies (e.g., hemophilia A). FVIII or sequence variants have been isolated, characterized, and cloned, as described in U.S. Pat. Nos. 4,757,006; 7,138,505, 5,004,804; 5,198,349, 5,250,421; 5,919,766; 2010/0081615; 2013/0017997 and 2013/0108629 each of which is incorporated herein by reference in its entirety.

"B domain" of Factor VIII, as used herein, is the same as the B domain known in the art that is defined by internal amino acid sequence identity and sites of proteolytic cleavage by thrombin, e.g., residues Ser741-Arg1648 of full length human factor VIII. The other human factor VIII domains are defined by the following amino acid residues: A1, residues Ala1-Arg372, A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. Preferably, the B domain of Factor VIII is deleted ("B domain deleted factor VIII" or "BDD FVIII"). An example of a BDD FVIII is REFACTO (recombinant BDD FVIII). The B domain of FVIII is discussed in U.S. Publ. No. 2013/0108629, which is incorporated herein by reference in its entirety.

A "B domain deleted factor VIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B domain deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, B domain deleted factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B domain deleted factor VIII is constructed with a deletion of amino acids 747-1638, i.e., virtually a complete deletion of the B domain. Hoeben R. C. et al, J. Biol. Chem. 265 (13): 7318-7323 (1990), incorporated herein by reference in its entirety. A. B domain deleted factor VIII may also contain a deletion of amino acids 771-1666 or amino acids 868-1562 of factor VIII. Meulien P., et al Protein Eng. 2(4): 301-6 (1988), incorporated herein by reference in its entirety. Additional B domain deletions that are part of the invention include, e.g.: deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions may be made in any Factor VIII sequence. B domain deletions of FVIII are disclosed in U.S. Publ. No. 2013/0108629, which is incorporated herein by reference in its entirety.

"Factor IX" and "FIX," as used herein, means functional Factor polypeptide in its normal role in coagulation, unless otherwise specified. Thus, the term Factor IX includes variant polypeptides that are functional and the polynucleotides that encode such functional variant polypeptides. Preferred Factor IX polypeptides are the human, bovine, porcine, canine, feline, and murine Factor IX polypeptides. The full length polypeptide and polynucleotide sequences of Factor IX are known, as are many functional variants, e.g., fragments, mutants and modified versions. Factor IX polypeptides include full-length Factor IX, full-length Factor IX minus Met at the N-terminus, full-length Factor IX minus the signal sequence, mature Factor IX (minus the signal sequence and propeptide), and mature Factor IX with an additional Met at the N-terminus. Factor IX is preferably made by recombinant means ("recombinant Factor IX" or "rFIX"), i.e., it is not naturally occurring or derived from plasma. FIX is disclosed in U.S. Publ. Nos. 2011/0046060 and 2013/0202595, each of which is incorporated herein by reference in its entirety.

In some embodiments, the recombinant polypeptide is an antibody. In some embodiments, the recombinant polypeptide is a monoclonal antibody. In some embodiments, the antibody is a humanized antibody. In some embodiments, the recombinant polypeptide is a chimeric antibody. In some embodiments, the recombinant polypeptide is any antibody disclosed in U.S. Pat. No. 7,300,773 which is incorporated herein by reference in its entirety.

In some embodiments, the recombinant polypeptide is a receptor. In some embodiments, the antibody is a receptor tyrosine kinase. In some embodiments, the receptor is any receptor disclosed in U.S. Pat. No. 7,300,773, which is incorporated herein by reference in its entirety.

In some embodiments the recombinant polypeptide is a growth factor or other signaling molecule. In some embodiments the recombinant polypeptide is a G-protein coupled receptor. In some embodiments the recombinant polypeptide is any polypeptide disclosed in U.S. Pat. No. 7,300,773.

In some embodiments, the recombinant polypeptide is produced by a host cell. In some embodiments, the recombinant polypeptide is produced by a eukaryotic host cell. In some embodiments, the recombinant polypeptide is produced by a mammalian host cell.

Abbreviations

AEX: anion exchange chromatography
CEX: cation exchange chromatography
CV: column volume
DF: diafiltration
DoE: design of experiments
HIC: hydrophobic interaction chromatography
HMW: high molecular weight aggregates
LMW: low molecular weight aggregates
HCP: host cell protein
Peak 1: clipped etanercept
Peak 2: native etanercept
Peak 3: misfolded etanercept
LRV: $Log_{10}$ (total impurity in load/total impurity in eluate)
CV: column volume
PS: pilot scale
OD: optical density
TSA: total sialic add
UF: ultrafiltration
WFI: water for injection By applying knowledge within the skill of those in the art, embodiments of the invention may be modified and/or adapted for various applications, without undue experimentation, without departing from the general concept of the present invention. Therefore, such adaptations and modifications are intended to be within the meaning and range of equivalents of the disclosed embodiments, based on the teaching and guidance presented herein.

EXAMPLES

Example 1

Enrichment of TSA and Removal of Impurities Through Use of a SE Hicap Column Summary A chromatography process was developed for the isolation/purification/enrichment of recombinant polypeptides with enhanced or increased levels of sialylation compared to recombinant polypeptides with decreased or lower levels of sialylation present in the same initial mixture.

The recombinant polypeptide utilized in this example is the TNFR-Fc fusion protein etanercept. Highly sialylated forms of recombinant polypeptides can represent a highly desirable class of therapeutically advantageous protein isoforms. The present example describes development of a robust process capable of enriching the content of recovered/isolated, highly sialylated forms of recombinant polypeptides while maintaining acceptable product recovery and yield. In this particular example, a process was developed wherein SE Hicap chromatography was used to recover/isolate highly sialylated forms of an Fc-fusion protein.

SE Hicap utilized in flow-through mode was selected primarily for its TSA enrichment potential, ability to reduce Peak 3 and aggregates, capability for robust DNA clearance, and ease of interface with the other process steps. SE Hicap enriches TSA by electrostatically repelling the negatively-charged sialylated etanercept into the flow-through, while retaining the more positively-charged (lesser sialylated) protein when run at a pH below its pI. It was found that load pH, load conductivity, and loading ratio are all key and critical parameters for this column. Process temperature, process flow rate, and resin ligand capacity had negligible impact on yield and product attributes under the conditions studied and were judged to be non-key-process parameters.

Materials

Solutions: The pH and conductivity of each buffer were verified before use.

Load Material and Adsorbent: All samples were frozen at −70° C. and thawed at ambient temperature prior to initiating chromatography. For all of the experiments, the load pH was adjusted with 1 M acetic acid, 1 M citric acid, or 2.4 M Tris base. Then, the load conductivity was adjusted with 1 M NaCl in acetate or citrate buffer. RO/DI water was added if the load conductivity was too high.

Chromatography Method

All columns were packed with a 20% compression factor to a packed bed height of 15 cm or 16 cm. The chromatography steps were carried out with an AKTA Explorer 900 (GE Healthcare Life Sciences) and the Unicorn interface software (version 5.11) at approximately 22° C. a down-flow mode. Throughout all of the development studies operated in flow-through mode, the chromatography method generally consisted of an equilibration step, a load step, a wash step to remove non-bound protein, a strip step to remove impurities for analysis, a cleaning step with 1 N NaOH and a storage step in 0.1 N NaOH. The cleaning and storage conditions for this step were not studied; rather these follow the manufacturer's recommendations. The wash fractions were pooled with the flow-through fractions unless otherwise noted. The flow-through, wash, and strip fractions were analyzed for yield and product attributes.

Resin Screening, Column Interfacing, and Buffer Matrix Method

Static binding capacity calculations were used to screen candidate CEX resins for their ability to bind protein. This was determined by buffer exchanging the candidate resins with equilibration buffer and then incubating the composition containing the Etanercept overnight with a known volume of candidate resins on a shaker. The mixtures of resin and protein were spun down and the supernatants were subsequently measured for A280. The resins with high static capacities were then packed in columns and further evaluated in bind/elute or flow-through mode. Product yield, aggregates, Peak 1, Peak 2, Peak 3, TSA, HCP, and DNA were measured to gauge separation performance. Resins with high capacities that had poor separation of product-related impurities during elution were further evaluated as a capture step, but eliminated as a polishing step. However, resins with low capacities that had good separation of impurities were further evaluated in flow-through mode, as was the case with SE Hicap.

SE Hicap was selected specifically for its ability to enrich TSA and remove aggregates, DNA, and some Peak 3 and HCP. In addition, SE Hicap in flow-through mode had no challenges interfacing with previous and subsequent purification steps, while eliminating need for any intermediate step. It was determined that acetate buffer was the most optimal buffer to be used in this process.

DOE Method

A DoE (central composite) study was designed to characterize the load ratio, load conductivity, and load pH, while a second DoE (screening) was designed to characterize the process temperature, resin capacity, and process flow rate. Both DoE studies were designed using Design Expert (version 8.0.6). Load ratio, load conductivity, and load pH were chosen as variables in the first DoE because earlier experiments showed that they had an impact on product yield and product attributes. Process temperature, resin capacity, and process flow rate were assessed in a separate DoE because earlier studies showed that these parameters had minimal effect on product yield and product attributes.

To perform regression analyses on the data, the results were entered into the Design Expert and analyzed first for normal distribution and outliers via Box Cox and Externally Studentized Residuals, respectively. If the data was not normally distributed, transformations were conducted (e.g., log 10) based on the software's recommendations. Any outliers that significantly weakened the models were omitted from the analysis. Afterwards, insignificant parameters (p-value>0.05) were removed using the backwards or manual elimination function to simplify the model. In a few cases, insignificant parameters were retained in the model to strengthen the R2 and lack of fit. All models were built on the assumption that only main effects and 2-level interactions would be significant and not be confounded.

Analytical Methods

The analytical methods utilized for all of the experiments are summarized in Table 2. The starting material is sufficiently pure that measurement of the product yield using OD280 method is accurate for the SE Hicap column.

TABLE 2

Summary of Analytical Methods

| Analytical Method | Measurement | Unit | Method Validation/Qualification Report Number(s) |
|---|---|---|---|
| $OD_{280}$ | Total absorbance in each fraction and total $A_{280}$ in the eluate | Non-dimensional | Not Applicable |
| Pressure | Column inlet pressure | Psig | AKTA program |
| $UV_{280}$ | Chromatograph | n/a | Not Applicable |
| HPLC-SEC | Non-reversible soluble aggregate | % | TD-TDMP-9032 |
| HPLC-HIC | Peak 1, Peak 2, and Peak 3 | % | TD-TDMP-242 |
| LC-90/GXII (Non-Reduced) | Purity and Highest Single Impurity | % | TD-TDMP-285 |
| LC-90/GXII (Reduced) | Purity and LMW | % | TD-TDMP-286 |
| HPLC-IEX | Total Sialic Acid (TSA) | Mole per mole | TD-TDMP-370 |
| iCIEF | Charged Heterogeneity | % | TD-TDMP-284 |
| ECL | Total Host Cell Protein | Parts per million (ppm) | TD-TDMP-252 |
| Q-PCR | Total DNA | Parts per billion (ppb) | TD-TDMP-321 |

DOE 1 (Central Composite)

The DoE study characterizing load ratio, load pH, and load conductivity was successfully completed without any deviations from the study design. A typical SE Hicap chromatogram under control conditions shows how the UV deflects with a pre-peak during the load, decreases in UV, and then increases in UV before reaching a plateau (FIG. 1). It was found that weak protein-binding can lead to insufficient TSA enrichment (data not shown). It was found that strong protein-binding can lead to product loss (data not shown).

Low load pH and low load conductivity decreased product yield, enriched TSA content, increased Peak 1 impurity, decreased aggregate level, and increased monomer content (Table 3 see also Table 4). Load pH and load conductivity have an interaction in that a low load pH can offset the effects of high load conductivity on these outputs and vice versa. As load conductivity or load pH increased, Peak 2 level decreased by the amount that was increased in Peak 3 level (Table 3, see also Table 4). This showed that varying load conductivity and load pH can change the relative distribution of Peaks 1, 2, and 3.

TABLE 3

DOE 1 (Central Composite) Data #1

| Cycle | Load Ratio (OD/mL resin) | Load Conductivity (mS/cm) | Load pH | Azso Yield (%) | HMW Aggregate (%) | Monomer (%) | Peak 1 (%) | Peak2 (%) | Peak3 (%) | NANA (mol/mol) | NGNA (mol/mol) | TSA (mol/mol) | Reduced Purity (%) |
|---|---|---|---|---|---|---|---|---|---|---|---|---|---|
| 1 | 40.9 | 9.0 | 5.8 | 66.9 | 3.4 | 96.7 | 4.9 | 60.0 | 34.3 | 15.5 | 0.0 | 15.6 | 95.1 |
| 2 | 54.6 | 9.0 | 5.8 | 71.1 | 4.0 | 96.0 | 4.7 | 60.1 | 34.2 | 15.4 | 0.1 | 15.5 | 94.9 |
| 3 | 27.1 | 9.0 | 5.8 | 58.1 | 2.8 | 97.2 | 4.5 | 63.2 | 31.4 | 15.8 | 0.1 | 15.9 | 94.3 |
| 4 | 49.0 | 11.0 | 6.3 | 87.9 | 8.7 | 91.3 | 4.0 | 53.5 | 41.5 | 14.5 | 0.1 | 14.6 | 95.2 |
| 5 | 32.7 | 11.0 | 6.3 | 83.9 | 8.4 | 91.6 | 4.5 | 54.1 | 40.4 | 14.7 | 0.1 | 14.8 | 95.3 |
| 6 | 49.0 | 11.0 | 5.3 | 65.0 | 2.4 | 97.6 | 4.8 | 63.8 | 30.1 | 15.9 | 0.1 | 16.0 | 94.2 |
| 7 | 32.7 | 11.0 | 5.3 | 58.5 | 1.8 | 98.2 | 4.6 | 64.5 | 30.3 | 15.9 | 0.1 | 16.0 | 94.0 |
| 8 | 40.9 | 9.0 | 5.8 | 63.3 | 3.6 | 96.4 | 4.5 | 60.9 | 33.5 | 15.3 | 0.1 | 15.4 | 94.8 |
| 9 | 40.9 | 9.0 | 5.8 | 62.9 | 3.4 | 96.6 | 4.5 | 61.7 | 33.0 | 16.0 | 0.1 | 16.1 | 94.9 |
| 10 | 40.9 | 12.4 | 5.8 | 78.1 | 7.7 | 92.3 | 4.1 | 55.7 | 39.3 | 14.5 | 0.1 | 14.6 | 95.5 |
| 11 | 40.9 | 5.6 | 5.8 | 45.1 | 2.1 | 97.9 | 5.4 | 66.1 | 27.8 | 16.7 | 0.1 | 16.8 | 94.4 |
| 12 | 32.7 | 7.0 | 6.3 | 63.5 | 5.8 | 94.2 | 5.0 | 59.7 | 33.9 | 16.1 | 0.1 | 16.3 | 94.9 |
| 13 | 49.0 | 7.0 | 6.3 | 67.0 | 4.4 | 95.6 | 4.3 | 58.3 | 36.4 | 15.5 | 0.1 | 15.6 | 95.2 |
| 14 | 49.0 | 7.0 | 5.3 | 28.5 | 1.8 | 98.2 | 7.4 | 70.5 | 20.5 | 17.7 | 0.1 | 17.8 | 92.3 |
| 15 | 32.7 | 7.0 | 5.3 | 13.7 | 0.0 | 100.0 | 12.9 | 67.3 | 16.5 | 18.5 | 0.1 | 18.6 | 86.3 |
| 16 | 40.9 | 9.0 | 5.0 | 21.5 | 0.0 | 100.0 | 9.9 | 70.8 | 17.0 | 18.2 | 0.1 | 18.3 | 89.7 |
| 17 | 40.9 | 9.0 | 6.6 | 82.9 | 8.2 | 91.8 | 4.5 | 54.5 | 39.9 | 14.8 | 0.1 | 14.9 | 95.2 |
| 18 | 40.9 | 9.0 | 5.8 | 67.6 | 3.6 | 96.4 | 4.0 | 62.9 | 32.5 | 15.9 | 0.1 | 16.1 | 95.1 |

TABLE 4

Effect of Load Ratio, Load pH and Load Conductivity on Yield, TSA, Aggregation, and Peak Size.

| Feed Source | Load Ratio (mg/mL) | Load pH | Load Conductivity (mS/cm) | A280 Yield (%) | TSA (mole/mole) | Aggregate (%) | Peak 1 (%) | Peak 2 (%) | Peak 3 (%) |
|---|---|---|---|---|---|---|---|---|---|
| C12-01 | 53 | 5.6 | 10 | 73.5 | 15.7 | 5.1 | 6.9 | 61 | 32.1 |
| C12-01 | 28 | 5.6 | 10 | 64.9 | 15.4 | 3.7 | 6.1 | 63.7 | 30.1 |
| C12-01 | 56 | 5.6 | 10 | 74.6 | 15.7 | 5.1 | 6.2 | 60.6 | 33.2 |
| ILS-003 | 53 | 5.8 | 11 | 78.5 | 15.4 | 8.1 | 5.8 | 63.1 | 31 |
| ILS-003 | 56 | 5.8 | 11 | 78.3 | 15.6 | 8.1 | 6 | 62.9 | 31.2 |
| ILS-003 | 53 | 5.6 | 10 | 70.2 | 16 | 4.5 | 6.5 | 66.6 | 27 |
| ILS-003 | 56 | 5.6 | 10 | 70.4 | 16.5 | 4.7 | 6.4 | 66.3 | 27.3 |

TABLE 5

DOE 1 (Central Composite) Data #2

| Cycle | Load Ratio (OD/mL resin) | Load Conductivity (mS/cm) | Load pH | Reduced LMW (%) | Non-Reduced Purity (%) | Non-Reduced Impurity (%) | HCP Content (ppm) | HCP Clearance (LRV) | DNA Content (ppb) | DNA Clearance (LRV) | Acidic Isoform (%) | Basic Isoform (%) | Main Isoform (%) |
|---|---|---|---|---|---|---|---|---|---|---|---|---|---|
| 1 | 40.9 | 9.0 | 5.8 | 2.6 | 96.2 | 3.8 | 1581 | 0.3 | 58.4 | 1.5 | 57.7 | 5.3 | 37.1 |
| 2 | 54.6 | 9.0 | 5.8 | 2.6 | 96.5 | 3.5 | 1590 | 0.3 | 39.6 | 1.7 | 58.7 | 5.4 | 36.0 |
| 3 | 27.1 | 9.0 | 5.8 | 3.2 | 96.7 | 3.3 | 1721 | 0.3 | 44.4 | 1.7 | 60.4 | 4.7 | 34.8 |
| 4 | 49.0 | 11.0 | 6.3 | 2.4 | 96.7 | 3.3 | 1416 | 0.2 | 190.5 | 0.9 | 60.4 | 5.1 | 34.5 |
| 5 | 32.7 | 11.0 | 6.3 | 2.3 | 96.4 | 3.6 | 1327 | 0.3 | 175.2 | 0.9 | 59.9 | 4.7 | 35.4 |
| 6 | 49.0 | 11.0 | 5.3 | 3.1 | 96.4 | 3.6 | 1446 | 0.3 | 40.0 | 1.7 | 56.6 | 6.9 | 36.5 |
| 7 | 32.7 | 11.0 | 5.3 | 3.4 | 96.5 | 3.5 | 1516 | 0.4 | 24.4 | 2.0 | 56.1 | 6.2 | 37.7 |
| 8 | 40.9 | 9.0 | 5.8 | 2.8 | 96.6 | 3.4 | 1719 | 0.3 | 42.7 | 1.7 | 58.7 | 6.0 | 35.4 |
| 9 | 40.9 | 9.0 | 5.8 | 2.8 | 96.6 | 3.4 | 1698 | 0.3 | 54.2 | 1.6 | 58.6 | 5.0 | 36.4 |
| 10 | 40.9 | 12.4 | 5.8 | 2.2 | 97.1 | 2.9 | 1561 | 0.2 | 64.6 | 1.4 | 57.2 | 6.2 | 36.6 |
| 11 | 40.9 | 5.6 | 5.8 | 3.7 | 96.7 | 3.3 | 2448 | 0.3 | 35.6 | 1.9 | 61.4 | 4.2 | 34.4 |
| 12 | 32.7 | 7.0 | 6.3 | 2.9 | 96.6 | 3.4 | 1834 | 0.3 | 86.0 | 1.4 | 59.2 | 5.2 | 35.7 |
| 13 | 49.0 | 7.0 | 6.3 | 2.7 | 91.5 | 8.5 | 1564 | 0.3 | 98.1 | 1.3 | 58.0 | 4.5 | 37.5 |
| 14 | 49.0 | 7.0 | 5.3 | 5.5 | 81.8 | 18.2 | 3024 | 0.4 | 11.7 | 2.6 | 63.4 | 4.4 | 32.2 |
| 15 | 32.7 | 7.0 | 5.3 | 11.0 | 88.4 | 11.6 | 6435 | 0.4 | 42.4 | 2.4 | 75.0 | 3.8 | 21.2 |
| 16 | 40.9 | 9.0 | 5.0 | 6.8 | 84.6 | 15.4 | 3644 | 0.4 | 21.3 | 2.5 | 66.5 | 5.0 | 28.5 |
| 17 | 40.9 | 9.0 | 6.6 | 2.2 | 96.8 | 3.2 | 1149 | 0.3 | 204.8 | 0.9 | 60.1 | 4.2 | 35.7 |
| 18 | 40.9 | 9.0 | 5.8 | 2.6 | 97.0 | 3.0 | 1387 | 0.3 | 39.1 | 1.7 | 57.0 | 5.2 | 37.8 |

A high load conductivity or high load pH decreased DNA clearance (Table 5). However, load pH decreased DNA clearance to a greater extent than conductivity. Also, a high load pH also decreased HCP clearance (Table 5).

Low load pH and low load conductivity decreased purity level (relative to all impurities) (Table 5). Load pH and load conductivity have an interaction in that a low load pH can offset the effects of high load conductivity on the purity level. As load conductivity or load pH increased, the highest single impurity level and LMW decreased (Table 5).

The negatively-charged acidic isoform was enriched at low conductivity and low pH, but reduced in concentration when the basic and main isoforms desorbed from the column at high conductivity or high pH (Table 5). Therefore, load pH and load conductivity have an interaction in that load pH can offset the effects of load conductivity on the isoforms.

These experiments indicate that the operating space for SE Hicap should have a load pH target of 5.6 with a range of 5.5-5.8, a load conductivity target of 10.0 mS/cm with a range of 9.5-11 mS/cm, and a load ratio target of 41 mg/mL resin with a range of 33-54 mg/mL resin. These load conditions would ensure that the flow-through/wash pool have TSA levels of 15-6.5 mole/mole, aggregate levels of <6%, Peak 1 levels of <6%, DNA clearance of ~1.5 LRV, and a sufficient product yield of 55-80%.

DoE 2 (Screening)

The DoE study characterizing process temperature, resin capacity, and process flow rate was successfully completed without any deviations from the protocol. The data from this DoE study are listed in Table 6. Although the most significant variables were resin capacity and process temperature, their impact on the product yield and product attributes were negligible. Thus, the process is robust and can tolerate a wide operating range for temperature, resin capacity, and flow rate.

TABLE 6

DOE 2 (Screening) Data.

| Cycle | Process Temperature (° C.) | Resin Capacity (mg Lysozyme/ mL resin) | Process Flow Rate (cm/hr) | $A_{280}$Yield (%) | TSA (mol/mol) | HMW Aggregate (%) | Monomer (%) | Peak 1 (%) | Peak 2 (%) | Peak 3 (%) |
|---|---|---|---|---|---|---|---|---|---|---|
| 1 | 26.0 | 125 | 75 | 76.8 | 14.6 | 4.6 | 95.4 | 4.2 | 63.8 | 32.0 |
| 2 | 26.0 | 158 | 150 | 74.4 | 14.5 | 4.9 | 95.1 | 4.5 | 62.4 | 33.1 |
| 3 | 26.0 | 125 | 150 | 73.6 | 14.0 | 4.6 | 95.4 | 4.6 | 63.1 | 32.3 |
| 4 | 26.0 | 158 | 75 | 72.9 | 14.5 | 4.7 | 95.3 | 4.5 | 62.6 | 32.9 |
| 5 | 16.0 | 125 | 150 | 69.1 | 14.4 | 4.1 | 95.9 | 4.2 | 64.7 | 31.1 |
| 6 | 16.0 | 158 | 75 | 71.0 | 14.8 | 4.2 | 95.8 | 4.3 | 64.3 | 31.4 |
| 7 | 16.0 | 158 | 150 | 70.0 | 14.7 | 4.3 | 95.7 | 4.3 | 64.4 | 31.3 |
| 8 | 16.0 | 125 | 75 | 68.7 | 14.4 | 4.1 | 95.9 | 4.5 | 65.0 | 30.5 |
| 9 | 21.0 | 142 | 113 | 72.4 | 14.7 | 4.3 | 95.7 | 4.9 | 64.2 | 30.9 |
| 10 | 21.0 | 142 | 113 | 71.5 | 14.7 | 4.3 | 95.7 | 4.9 | 64.2 | 30.9 |
| 11 | 21.0 | 142 | 113 | 72.4 | 13.6 | 4.4 | 95.6 | 4.9 | 64.6 | 30.5 |
| 12 | 21.0 | 142 | 113 | 71.5 | 14.5 | 4.3 | 95.7 | 5.1 | 64.1 | 30.8 |

The SE Hicap flow-through chromatography was successfully developed a the second purification step to enrich TSA levels to 15-16.5 mole/mole, decrease aggregates by ~12%, and reduce DNA by ~1.5 LRV, while maintaining high product recoveries of 55-75% (A280) under target operating conditions. To meet these key and critical product attributes, the recommended operating space for SE Hicap would have a load pH target of 5.6±0.2, a load conductivity target of 10.0 mS/cm with a range of 9.5-11 mS/cm, and a load ratio target of 41 mg/mL resin±8 mg/mL resin based on DoE results. Other process parameters such as process temperature, process flow rate, and resin capacity had negligible impact on product yield and product attributes.

Example 2

Enrichment of TSA Using CEX Resin

Having determined the enrichment parameters for the SE Hicap CEX resin, the operating conditions necessary to enrich TSA while removing aggregates and/or misfolds was determined for other CEX resins. The resins tested were: GE SPXL, GE SP Sepharose, Millipore Eshmuno S, Tosoh Gigacap CM, Tosoh Gigacap S-650, and BioRad Nuvia S. The final operating conditions for each column can be seen below in Table 7:

TABLE 7

Operating Conditions for CEX Columns.

| Columns | pH | Conductivity (mS/cm) | Yield (%) | TSA Enriched (mole/mole) | Aggregate Removed (%) | Misfolds Removed (%) |
|---|---|---|---|---|---|---|
| SE Hicap Control | 5.6 | 10 | 47.9 | 3.1 | 21.2 | 15.8 |
| SP Sepharose | 5 | 9 | 44.0 | 2.3 | 9.5 | 26.8 |
| SP Sepharose XL | 5 | 6 | 53.3 | 2.2 | 7.3 | 16.0 |
| Nuvia S | 5 | 9 | 47.6 | 3.8 | 17.6 | 12.7 |
| Eshmuno S | 5 | 9 | 55.0 | 2.5 | 16.7 | 13.7 |
| GigaCap S | 5 | 8 | 46.9 | 3.9 | 20.3 | 13.7 |
| GigaCap CM | 5 | 6 | 40.1 | 4.0 | 22.5 | 20.7 |

A comparison of the enrichment of TSA by each column, with the results normalized to 50% of product yield, can be seen in FIG. 2. A comparison of the aggregates and misfolds removed by each column, with the results normalized to 50% of product yield, can be seen in FIG. 3.

The present invention is not limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method for enriching levels of sialylated Fc fusion polypeptides comprising a ligand binding domain of a receptor, the method comprising:
   contacting a composition which comprises an initial population of Fc fusion polypeptides having different levels of sialylation with a cation exchange chromatography (CEX) medium operated in a flow-through mode;
   wherein the contacting occurs at pH 5-6 and a conductivity of 8-12 mS/cm,
   wherein Fc fusion polypeptides that do not bind the CEX medium are separated from Fc fusion polypeptides that bind the CEX medium,
   wherein the Fc fusion polypeptides that do not bind the CEX medium comprise a higher level of sialylation compared to the bound Fc fusion polypeptides,
   wherein the Fc fusion polypeptides that do not bind the CEX medium comprise a total sialic acid content of 14-17 moles of sialic acid per mole of protein.

2. A method for enriching levels of sialylated Fc fusion polypeptides comprising a ligand binding domain of a receptor, the method comprising:
   a) contacting a composition which comprises an initial population of Fc fusion polypeptides having different levels of sialylation with a cation exchange chromatography (CEX) medium operated in a flow-through mode, wherein the contacting occurs at pH 5-6 and a conductivity of 8-12 mS/cm; and
   b) separating Fc fusion polypeptides that do not bind the CEX medium from Fc fusion polypeptides that bind the CEX medium,
   wherein the Fc fusion polypeptides that do not bind the CEX medium that are recovered comprise a higher level of sialylation compared to the bound Fc fusion polypeptides,
   wherein the Fc fusion polypeptides that do not bind the CEX medium comprise a total sialic acid content of 14-17 moles of sialic acid per mole of protein.

3. A method for enriching levels of sialylated Fc fusion polypeptides comprising a ligand binding domain of a receptor, the method comprising:
   a) contacting a composition which comprises an initial population of Fc fusion polypeptides having different levels of sialylation with a cation exchange chromatography (CEX) medium operated in a flow-through mode, wherein the contacting occurs at pH 5-6 and a conductivity of 8-12 mS/cm;
   b) separating Fc fusion polypeptides that do not bind the CEX medium from Fc fusion polypeptides that bind the CEX medium; and
   c) recovering the Fc fusion polypeptides that do not bind the CEX medium,
   wherein the Fc fusion polypeptides that do not bind the CEX medium comprise a higher level of sialylation compared to the bound Fc fusion polypeptides,
   wherein the Fc fusion polypeptides that do not bind the CEX medium comprise a total sialic acid content of 14-17 moles of sialic acid per mole of protein.

4. A method for enriching levels of sialylated Fc fusion polypeptides comprising a ligand binding domain of a receptor, the method comprising:
   a) providing a composition which comprises an initial population of Fc fusion polypeptides having different levels of sialylation;
   b) contacting the composition with a cation exchange chromatography (CEX) medium operated in a flow-through mode, wherein the contacting occurs at pH 5-6 and a conductivity of 8-12 mS/cm;
   c) separating Fc fusion polypeptides that do not bind the CEX medium from Fc fusion polypeptides that bind the CEX medium; and
   d) recovering the Fc fusion polypeptides that do not bind the CEX medium,
   wherein the Fc fusion polypeptides that do not bind the CEX medium comprise a higher level of sialylation compared to the bound Fc fusion polypeptides,
   wherein the Fc fusion polypeptides that do not bind the CEX medium comprise a total sialic acid content of 14-17 moles of sialic acid per mole of protein.

5. The method of claim 1, further comprising recovering the Fc fusion polypeptides that do not bind the CEX medium.

6. The method of claim 1, wherein the total sialic acid content of the Fc fusion polypeptides that do not bind the CEX medium is between 0.5 and 6 moles of sialic acid per mole of protein higher than that of the initial population of Fc fusion polypeptides.

7. The method of claim 6, wherein the total sialic acid content of the Fc fusion polypeptides that do not bind the CEX medium is between 0.5 and 4 moles of sialic acid per mole of protein higher than that of the initial population of Fc fusion polypeptides.

8. The method of claim 1, wherein the total sialic acid content of the Fc fusion polypeptides that do not bind the CEX medium is between 5% and 100% higher than that of the initial population of Fc fusion polypeptides.

9. The method of claim 8, wherein the total sialic acid content of the Fc fusion polypeptides that do not bind the CEX medium is between 5% and 40% higher than that of the initial population of Fc fusion polypeptides.

10. The method of claim 1, wherein the total sialic acid content of the initial population of Fc fusion polypeptides is 10 to 14 moles of sialic acid per mole of protein.

11. The method of claim 10, wherein the total sialic acid content of the initial population of Fc fusion polypeptides is 13-14 moles of sialic acid per mole of protein.

12. The method of claim 1, wherein the receptor is a TNF receptor.

13. The method of claim 12, wherein the Fc fusion polypeptide is etanercept.

14. The method of claim 1, wherein the contacting occurs at a load ratio between 30 and 100 mg total protein/ml CEX medium.

15. The method of claim 14, wherein the contacting occurs at a load ratio between 33 and 54 mg total protein/ml CEX medium.

16. The method of claim 15, wherein the contacting occurs at a load ratio of at least 41 mg total protein/ml CEX medium.

17. The method of claim 1, wherein contacting occurs at a pH of 5.3-5.8.

18. The method of claim 1, wherein the contacting occurs at a conductivity of at least 10 mS/cm.

19. The method of claim 1, wherein the Fc fusion polypeptides that do not bind the CEX medium comprise 25% to 80% of the initial population of Fc fusion polypeptides.

20. The method of claim 19, wherein the Fc fusion polypeptides that do not bind the CEX medium comprise 55% to 80% of the initial population of Fc fusion polypeptides.

21. The method of claim 1, wherein the CEX medium comprises a ligand selected from the group consisting of sulfoethyl; sulphopropyl; sulfopropyl; $CH_2—SO_3^-$; $CH_2CH_2CH_2SO_3^-$; $SO_3^-$; and $CH_2—COO^-$.

22. The method of claim 21, wherein the CEX medium comprises a sulfoethyl ligand.

23. The method of claim 22, wherein the CEX medium comprises a binding capacity of between 120 and 160 mg lysozyme/ml resin.

24. The method of claim 1, wherein the Fc fusion polypeptide is produced by a eukaryotic host cell.

25. The method of claim 24, wherein the eukaryotic host cell is a mammalian host cell.

26. The method of claim 1, wherein the contacting is performed at a manufacturing scale.

27. The method of claim 1, wherein the composition further comprises at least one impurity.

28. The method of claim 27, wherein the impurity comprises a DNA, RNA, lipid or protein.

29. The method of claim 28, wherein the impurity comprises a protein.

30. The method of claim 29, wherein the protein impurity comprises a truncated form of the Fc fusion polypeptide, an aggregated form of the Fc fusion polypeptide, or a misfolded form of the Fc fusion polypeptide.

31. The method of claim 27, further comprising providing a final composition comprising the Fc fusion polypeptides that do not bind the CEX medium, wherein the final composition comprises less impurities than the composition that comprised the initial population of Fc fusion polypeptides.

32. The method of claim 1, wherein contacting occurs at a pH of 5.5-5.8.

33. The method of claim 1, wherein the contacting occurs at a conductivity of 9.5-11.0 mS/cm.

34. The method of claim 1, wherein the Fc fusion polypeptides that do not bind the CEX medium comprise a total sialic acid content of 14.1-16.2 moles of sialic acid per mole of protein.

* * * * *